| United States Patent [19] | [11] Patent Number: 4,514,544 |
| Takahashi et al. | [45] Date of Patent: Apr. 30, 1985 |

[54] PAPER SIZING AGENT COMPRISED OF REACTION PRODUCT OF MALEIC ANHYDRIDE AND PROPYLENE OLIGOMERS

[75] Inventors: Yoshio Takahashi; Takeshi Shoji, both of Kanagawa, Japan

[73] Assignee: Mitsubishi Oil Company, Limited, Japan

[21] Appl. No.: 558,238

[22] Filed: Dec. 5, 1983

[51] Int. Cl.$^3$ .................. C08F 222/04; C08F 8/12
[52] U.S. Cl. ................... 525/327.4; 526/272
[58] Field of Search ............... 526/272; 525/327.4

[56] References Cited

U.S. PATENT DOCUMENTS

| 2,565,147 | 8/1951 | Pfluger | 526/272 |
| 3,532,672 | 10/1970 | Takahara | 526/272 |
| 3,580,893 | 5/1971 | Heilman | 525/327.4 |
| 4,071,581 | 1/1978 | Yokoyama | 526/272 |
| 4,152,312 | 5/1979 | Sackmann et al. | 526/272 |
| 4,161,571 | 7/1979 | Yasui et al. | 526/272 |

*Primary Examiner*—Joseph L. Schofer
*Assistant Examiner*—Peter F. Kulkosky
*Attorney, Agent, or Firm*—Sughrue, Mion, Zinn, Macpeak and Seas

[57] ABSTRACT

A paper sizing agent is disclosed. The sizing agent is obtained by alkali saponification of a reaction product which is obtained by reacting a propylene oligomer with maleic anhydride under heating in the absence of a catalyst. The propylene oligomer contains substantially no oligomers having 10 or less carbon atoms. Further, the content of oligomers having 11 to 12 carbon atoms is 0 to 30% by volume, the content of oligomers having 13 to 15 carbon atoms is 20 to 95% by volume and the content of oligomers having 16 to 21 carbon atoms is 5 to 50% by volume. The paper sizing agent provides a homogeneous transparent sizing agent, which restrains the amount of the foaming and also has improved sizing effects.

12 Claims, No Drawings

4,514,544

PAPER SIZING AGENT COMPRISED OF REACTION PRODUCT OF MALEIC ANHYDRIDE AND PROPYLENE OLIGOMERS

FIELD OF THE INVENTION

This invention relates to a paper sizing agent and, more particularly, it relates to a paper sizing agent which shows a sizing effect superior to a rosin type sizing agent while hardly foaming during use.

BACKGROUND OF THE INVENTION

Hitherto, as an internal sizing agent, a so-called rosin type sizing agent which employs rosin as raw material has been generally used. However, rosin is a natural substance and has some problems such as fluctuation of price, instability of supply and the like. Therefore, as synthesized sizing agents which take the place of this, so-called petroleum resin sizing agents which employ, as raw material, petroleum resin obtained from a mixture of $C_5$ and $C_9$ fractions which can be obtained from naphtha cracked oil and other various synthesized sizing agents have been proposed.

However, until several years ago, such synthesized sizing agents, except the petroleum resin sizing agent, were hardly put to practical use due to problems related to efficiency or price, and the petroleum resin sizing agent practically used was also limited in use due to problems related to efficiency.

However, recently substantial use has been made of synthesized sizing agents superior in efficiency and price to the rosin type sizing agent. Such agents are the water-soluble salt of alkenyl succinic acid which is made from a highly branched olefin and maleic anhydride. The paper sizing process using the water-soluble salt of alkenyl succinic acid as internal sizing agent has been well-known as described in Japanese Patent Publication No. 565/65 (corresponding to U.S. Pat. No. 3,139,373).

The water-soluble salt of alkenyl succinic acid has been said to have a problem in practical use due to foaming as described in Japanese Patent Publication (unexamined) No. 27003/79. The present inventors have found that the foam is formed only when the sizing agent is obstructed from fixing on pulp during sizing and the unfixed water-soluble salt of alkenyl succinic acid or a reaction product of alkenyl succinic acid with aluminum sulfate remains in a pulp slurry. Thus, the present inventors found that when fixing proceeds normally, there is no problem in practical use since there is almost no foaming. The undesirable obstruction to fixing of the sizing agent on pulp is herein referred to as "fixing obstruction".

However, though the obstruction to fixing of the sizing agent in the paper making process is a rare phenomenon, the foaming phenomenon caused by the unfixed sizing agent consisting of the water-soluble salt of alkenyl succinic acid gives a serious damage for its process and the quality of the produced paper.

SUMMARY OF THE INVENTION

Thus, as a result of the earnest studies to develop a synthesized sizing agent which shows a sizing effect superior to the rosin type sizing agent and which hardly foams even if it receives the fixing obstruction in its using, the present inventors have found that the sizing effect and foaming nature of the water-soluble salt of alkenyl succinic acid are remarkably different depending on the molecular structure of the olefins used as raw material, and that the oligomer of propylene is the best raw material among the branched olefins. Moreover, as a result of detailed studies on the sizing effect and foaming nature with respect to the alkali-saponified product of the reaction product of a highly branched propylene oligomer with maleic anhydride, the present inventors have also found that the smaller the carbon number of the raw propylene oligomer, the more remarkable the foaming in receiving the fixing obstruction. In particular, it was found that the sizing agent obtained by alkali saponification of the reaction product of an oligomer having 10 carbon atoms or less with maleic anhydride shows a remarkable foaming. On the other hand, it was also found that the reaction product of an oligomer having 16 to 21 carbon atoms alone and maleic anhydride neither becomes a homogeneous transparent sizing agent nor affords a satisfactory sizing effect. However, when the sizing agent obtained from propylene oligomer having 16 to 21 carbon atoms was mixed in a particular amount with a sizing agent obtained from an oligomer having 11 to 15 carbon atoms, it affords a homogeneous transparent sizing agent, which restrains the foaming and also has an effect on improving the sizing effect.

As a result of further studies based on the knowledge obtained from these results, the present inventors have found that a sizing agent which is obtained by alkali saponification of a reaction product of a propylene oligomer (oligomers having 10 or less carbon atoms are substantially removed, the content of oligomers having 11 to 12 carbon atoms is selected in a particular amount or less and oligomers having 16 to 21 carbon atoms are contained only in the amount of particular range) with maleic anhydride shows a sizing effect superior to the rosin type sizing agent over a wide range of addition amount. Further, such a sizing agent causes substantially no foaming when it receives fixing obstruction.

The sizing agent related to this invention is a paper sizing agent. The agent is obtained by alkali saponification of the reaction product of a highly branched propylene oligomer with maleic anhydride. The oligomer does not substantially contain the oligomers having 10 or less carbon atoms and is a propylene oligomer in which the content of the oligomers having 11 to 12 carbon atoms is 0 to 30% by volume (measured by the method described in ASTM D2424), the content of the oligomers having 13 to 15 carbon atoms is 20 to 95% by volume (measured by the method described in ASTM D2424) and the content of the oligomers having 16 to 21 carbon atoms is 5 to 50% by volume (measured by the method described in ASTM D2424).

This sizing agent has a sizing effect superior to the rosin type sizing agent over a wide range of addition amount. Further, this sizing agent does not substantially cause the foaming when it receives fixing obstruction.

DETAILED DESCRIPTION OF THE INVENTION

The oligomers of propylene are in general a mixture of highly branched monoolefins which can be obtained by polymerization of propylene in the presence of an acid catalyst such as phosphoric acid and the like or a Friedel-Crafts catalyst such as aluminum chloride and the like. The oligomer of propylene used in this invention is a oligomer having an average molecular weight of 175 to 250, preferably 180 to 245, in which oligomers having 10 or less carbon atoms are substantially removed (2% by volume or less) by atmospheric distillation or vacuum distillation of these propylene oligomers. If necessary, the oligomer used in this invention is subjected to the fractional distillation and the mixing treatments to remove the oligomers having 10 or less carbon atoms and to obtain the oligomer reblended to the composition formulated herein. The content of the oligomers having 11 to 12 carbon atoms measured by the method described in ASTM D2424 is 0 to 30% by volume, preferably 0 to 20% by volume. The content of the oligomers having 13 to 15 carbon atoms measured by the method described in ASTM D2424 is 20 to 95% by volume, preferably 40 to 90% by volume, and the content of the oligomers having 16 to 21 carbon atoms measured by the method described in ASTM D2424 is 5 to 50% by volume, preferably 10 to 40% by volume. It is desired that the oligomers having 10 or less carbon atoms are not present at all. However, it is difficult to remove them completely by distillation, and thus if the content is 2% by volume or less, the purpose of this invention can be achieved. Accordingly, in this invention, "does not substantially contain the oligomers having 10 or less carbon atoms" means that their content is 2% by volume or less. When the content of the oligomers having 11 to 12 carbon atoms exceeds 30% by volume, the foaming is formed if fixing obstruction should occur though the sizing effect does not change. When the content of the oligomers having 16 to 21 carbon atoms is less than 5% by volume, restraint of the foaming and improvement of the sizing effect are little caused. However, when it exceeds 50% by volume, the foaming becomes small but a satisfactory sizing effect cannot be obtained.

As described above, Japanese Patent Publication No. 565/65 (corresponding to U.S. Pat. No. 3,139,373) proposes a water-soluble salt of alkenyl succinic acid as an internal sizing agent. The publication indicates that the water-soluble salt of alkenyl succinic acid which has an alkenyl group having 8 to 15 carbon atoms gives sizing properties, but those having an alkenyl group of 16 or more carbon atoms do not afford a satisfactory sizing effect. The reaction product of the propylene oligomer having 16 or more carbon atoms and maleic anhydride also does not easily form a homogeneous transparent sizing agent because it changes to an emulsion state when subjected to alkali saponification, and the sizing effect is remarkably inferior to the rosin type sizing agent.

This invention makes use of the undesirable propylene oligomer having 16 to 21 carbon atoms. The propylene oligomer used in the present invention does not substantially contain oligomers having 10 or less carbon atoms and is a propylene oligomer in which the content of the oligomers having 11 to 12 carbon atoms, the content of the oligomers having 13 to 15 carbon atoms and the content of the oligomers having 16 to 21 carbon atoms are suitably selected. The sizing agent obtained by alkali saponification of the reaction product of these propylene oligomers used in the present invention with maleic anhydride shows an improvement in the sizing effect and prevention of foaming due to fixing obstruction by the presence of the alkali saponification product of the reaction product of the oligomers having 16 to 21 carbon atoms with maleic anhydride. Thus, the sizing agent is apparently different from the water-soluble salt of alkenyl succinic acid having an alkenyl group containing 8 to 15 carbon atoms which is described in Japanese Patent Publication No. 565/65 (corresponding to U.S. Pat. No. 3,139,373).

Sizing agents which show little foaming during use include those using a hydrocarbon fraction which is obtained by acid treatment of butadiene as raw material (refer to Japanese Patent Publication (unexamined) No. 42405/79) and those using a hydrocarbon fraction which is obtained by acid treatment of the fraction of a boiling point 20° to 80° C. containing a chain conjugated diolefin having 5 carbon atoms which is by-produced by thermal decomposition, steam decomposition, contact decomposition and the like of a petroleum fraction as raw material (refer to Japanese Patent Publication (unexamined) No. 27003/79). However, these utilize a polymerized product of the diolefin having 4 or 5 carbon atoms as raw material and are apparently different from the sizing agent of this invention using the oligomer obtained from propylene which is a monoolefin having 3 carbon atoms as raw material.

The reaction product of the oligomer of propylene with maleic anhydride used in this invention can be obtained by heating the propylene oligomer and maleic anhydride in the absence of a catalyst, preferably in an inert atmosphere such as nitrogen under atmospheric pressure or some increased pressure, at 180° C. to 250° C., preferably at 200° C. to 230° C., followed by reacting at the same temperature for 1 to 30 hours, preferably for 3 to 20 hours. This reaction is required to be conducted in the absence of a catalyst, and when a radical polymerization initiator is used, copolymers are formed, which do not show a satisfactory sizing effect. The mol ratio of the oligomer to the maleic anhydride is not limited particularly, but is preferably used in an amount of 0.5 to 3 mol per mol of the oligomer. After the reaction is over, the unreacted oligomer and maleic anhydride are removed by distillation to afford a liquid reaction product having rather low viscosity. The saponification value (JIS K5902) of the reaction product is about 300 to 440. Depending on the reaction conditions a small amount of by-product may be formed. The by-product can be removed as a distillation residue by distillation under reduced pressure, but amount of by-product is small and its removal is not always required. The reaction product thus obtained is saponified by alkali and made a transparent solution to afford the sizing agent of this invention.

Examples of the alkali used for saponification in this invention include alkali metal hydroxides such as sodium hydroxide, potassium hydroxide and the like, ammonia, or water-soluble amines such as trimethylamine, diethylamine and the like, but the use of sodium hydroxide or potassium hydroxide is desirable. The amount of alkali used for saponification is 0.8 to 1.2 times, preferably 0.9 to 1.1 times, the amount corresponding to the saponification value of the reaction product of the oligomer and maleic anhydride. The foaming properties of the obtained sizing agent increase with the decrease of the amount of alkali, and when the amount is less than 0.8 time the amount corresponding to the saponification value, the sizing effect is not influenced but the foaming increases rather substantially.

The sizing agent related to this invention can be obtained from the oligomers which are adjusted so that the content of the oligomer having 11 to 12 carbon atoms, the content of the oligomers having 13 to 15 carbon atoms, and the content of the oligomers having 16 to 21 carbon atoms among the propylene oligomers may be a suitable ratio.

The agent can also be obtained by reacting the oligomers having 11 to 12 carbon atoms, 13 to 15 carbon atoms, and 16 to 21 carbon atoms independently with maleic anhydride and then mixing the resulting reaction products in a suitable ratio followed by saponification, or saponification followed by mixing. In this case, the amounts of each reaction product obtained by independently reacting these oligomers having 11 to 12 carbon atoms, 13 to 15 carbon atoms and 16 to 21 carbon atoms with maleic anhydride are 0 to 30% by volume, 20 to 95% by volume and 5 to 50% by volume, respectively.

The sizing agent related to this invention can be added to paper stock in a spontaneous process in the same manner as that of the conventional rosin type sizing agent. For example, it can be fixed on the pulp by adjusting the pH to about 4.0 to 5.5, preferably 4.2 to 5.0, by adding aluminum sulfate after adding the sizing agent related to this invention to the pulp slurry which is in or after the heating process. The agent of this invention can be used together with other sizing agents such as a conventional rosin type sizing agent, a petroleum resin sizing agent and the like in any ratio, and also may be used for surface sizing.

In the case of internal sizing, the used amount (addition amount) of the sizing agent related to this invention is in the range of 0.01 to 5.0% by weight, preferably 0.05 to 3.0% by weight, based on the weight of the dry pulp, and in the case of surface sizing, the sizing agent is coated in the amount of 0.005 to 0.5 g/m² on a dry weight basis.

As explained above, the propylene oligomer which is used as the raw material of the sizing agent related to this invention contains 5 to 50% by volume of propylene oligomer having 16 or more carbon atoms which is said not to afford a satisfactory sizing agent when reacted with maleic anhydride. However, the sizing agents of this invention which can be obtained by alkali saponification of the reaction product of a specific oligomer and maleic anhydride provide the excellent sizing effect without causing the foaming in receiving the fixing obstruction compared with a rosin type sizing agent.

The characteristics of the sizing agent related to this invention are described above. This invention is further concretely illustrated by the following Comparative Examples and Examples. However, the scope of the invention is not limited to these Examples.

COMPARATIVE EXAMPLE 1

A propylene oligomer obtained in a polymerization unit of propylene using phosphoric acid as catalyst was subjected to fractional distillation by atmospheric distillation to afford the starting oils A, B and C indicated in Table 1.

Next, 338 parts by weight of the starting oil A and 196 parts by weight of maleic anhydride were heated to 215° C. in an autoclave under nitrogen atmosphere and reacted for 7 hours in the absence of a catalyst. After the reaction, the reaction mixture was taken out and the unreacted propylene oligomer and maleic anhydride were removed by distillation under reduced pressure to afford 384 parts by weight of a yellowish brown oily reaction product. The saponification value of this reaction product was 421. The potassium hydroxide corresponding to the saponification value of the reaction product and water were added to the obtained reaction product, and the reaction mixture was stirred for 2 hours at 90° C. and saponified to give a transparent sizing agent containing 40% by weight of the solid component (Sizing Agent A). The pH of this sizing agent was 10.1.

TABLE 1

| Carbon Atoms in Oligomer | Content of Oligomer | | |
|---|---|---|---|
| | Starting Oil A (vol %) | Starting Oil B (vol %) | Starting Oil C (vol %) |
| 11–12 | 95.2 | 0 | 0 |
| 13–15 | 4.8 | 96.8 | 0 |
| 16–21 | 0 | 3.2 | 100.0 |
| Number Average Molecular Weight | 169 | 207 | 255 |

(The measurement of carbon number distribution was made by ASTM D2424.)

COMPARATIVE EXAMPLE 2

The starting oil B of Table 1 (311 parts by weight) and maleic anhydride (176 parts by weight) were reacted in the same manner as described in Comparative Example 1 and the unreacted reactants were removed to afford 321 parts by weight of a yellowish brown oily reaction product. The saponification value of this reaction product was 370. This product was saponified by the same manner as described in Comparative Example 1 to give a transparent sizing agent containing 40% by weight of the solid component (Sizing Agent B). The pH of this sizing agent was 10.2.

COMPARATIVE EXAMPLE 3

The starting oil C of Table 1 (332 parts by weight) and maleic anhydride (166 parts by weight) were reacted in the same manner as described in Comparative Example 1 and the unreacted reactants were removed to afford 300 parts by weight of a yellowish brown oily reaction product. The saponification value of this reaction product was 320. This product was saponified in the same manner as described in Comparative Example 1 and adjusted so as to have 40% by weight of the solid component. The product was in an emulsified state and a homogeneous transparent sizing agent could not be formed. The pH of this emulsified sizing agent (Sizing Agent C) was 10.1. Furthermore, potassium hydroxide was gradually added till the pH reached 11, but it did not become a homogeneous transparent solution.

COMPARATIVE EXAMPLE 4

The sizing test of the Sizing Agents A, B and C which were obtained in the above-mentioned Comparative Examples 1 to 3 was carried out. As a sizing agent for comparison, a commercial reinforced rosin sizing agent was used. The testing method was as follows.

A 3% slurry of hardwood bleached kraft pulp which was adjusted to the beating degree C.F.=400 cc was prepared and to this slurry was added Sizing Agent A, Sizing Agent B, Sizing Agent C or the reinforced rosin sizing agent in the proportion of 0.3% by weight, 0.5% by weight or 1% by weight (as solid component) based on the weight of dry pulp. Aluminum sulfate was added with stirring to make the pH of the slurry 4.5. The pulp slurry was diluted with water adjusted to pH 5.0 by aluminum sulfate to make the pulp concentration about 0.2% by weight. The pulp was then made into paper by a TAPPI standard sheet machine according to the general method. After pressing for dehydration (4 kg/cm²×1 min), the wet paper was dried by a rotary dryer for 3 minutes at 105° C. The basis weight of this hand-made paper corresponded to 60 g/m².

The obtained paper was allowed to stand in a room at a temperature of 20° C. and 65% humidity for 24 hours, and then the sizing degree was measured by JIS-P-8122 Stöckigt sizing degree testing method. The results are summarized in Table 2.

Next, in order to examine the foaming under the conditions in which the pulp slurry concentration was low and the sizing agent readily received the fixing obstruction, a 0.8% by weight slurry of hardwood bleached kraft pulp which was adjusted to the beating degree C.F.=400 cc was added with Sizing Agent A, Sizing Agent B, Sizing Agent C, or reinforced rosin sizing agent in a proportion of 0.5% by weight (as solid component) based on the weight of dry pulp, and aluminum sulfate was added to make the pulp slurry pH 4.5. Then, 500 ml of this pulp slurry was taken into a 1 l of Erlenmeyer flask and sealed. It was attached to a horizontal reciprocating shaker (shaking frequency 156 shaking/min, amplitude 70 mm) and shaken for 1 minute. Then, the volume of foam in the pulp slurry was measured by the Boadway bubble measuring scale (Pulp and Paper Engineering, Vol. 2, No. 11, p. 22). The results are summarized in Table 2.

TABLE 2

| Sizing Agent | Stockigt Sizing Degree (sec) | | | Foam Content (% by volume) |
| --- | --- | --- | --- | --- |
| | 0.3* | 0.5* | 1.0* | 0.5* |
| A | 17.4 | 26.5 | 32.5 | 0.44 |
| B | 18.1 | 27.0 | 33.5 | 0.37 |
| C | 0 | 2.0 | 7.1 | 0.06 |
| Reinforced Rosin Sizing Agent | 10.3 | 22.0 | 32.0 | 0.31 |

Note:
*Addition amount of sizing agent (% by weight)

In the Sizing Agent A obtained from the propylene oligomer which is mainly composed of the oligomers having 11 to 12 carbon atoms and does not contain any oligomers having 16 or more carbon atoms and the Sizing Agent B obtained from the propylene oligomer which does not contain the oligomers having 11 to 12 carbon atoms but is mainly composed of the oligomers having 13 to 15 carbon atoms and contains less than 5% by volume of the oligomers having 16 or more carbon atoms, both Sizing Agents A and B indicate a sizing effect equal to or superior to the reinforced rosin sizing agent. However, the amount of foam is larger than that of the reinforced rosin sizing agent. In the emulsified Sizing Agent C obtained from only the propylene oligomer having 16 or more carbon atoms, the amount of the foaming is less than that of the reincorced rosin sizing agent. However, the sizing effect is apparently far inferior to the reinforced rosin sizing agent.

EXAMPLE 1

The starting oils B and C, or A, B and C of Table 1 which were obtained in Comparative Example 1 were mixed to afford the starting oils D, E, F and G indicated in Table 3.

Next, 424 parts by weight of this starting oil D was reacted with 235 parts by weight of maleic anhydride in the same manner as described in Comparative Example 1 and the unreacted reactants were removed to afford 431 parts by weight of a reaction product. The saponification value of this reaction product was 367. This product was saponified in the same manner as described in Comparative Example 1 to afford a transparent sizing agent related to this invention containing 40% by weight of the solid component (Sizing Agent D). The pH of this sizing agent was 10.2.

TABLE 3

| Carbon Atoms in Oligomer | Content of Oligomer | | | |
| --- | --- | --- | --- | --- |
| | Starting Oil D (vol %) | Starting Oil E (vol %) | Starting Oil F (vol %) | Starting Oil G (vol %) |
| 11–12 | 0 | 19.0 | 36.2 | 9.5 |
| 13–15 | 87.1 | 49.4 | 32.8 | 30.5 |
| 16–21 | 12.9 | 31.6 | 31.0 | 60.0 |
| Number Average Molecular Weight | 212 | 214 | 207 | 232 |

(The measurement of carbon number distribution was made by ASTM D2424.)

EXAMPLE 2

The starting oil E of Table 3 (321 parts by weight) and maleic anhydride (176 parts by weight) were reacted in the same manner as described in Comparative Example 1 and the unreacted reactants were removed to afford 325 parts by weight of a yellowish brown oily reaction product. The saponification value of this reaction product was 369. This product was saponified in the same manner as described in Comparative Example 1 to give a transparent sizing agent related to this invention containing 40% by weight of the solid component (Sizing Agent E-1). The pH of this sizing agent was 10.1.

EXAMPLE 3

The starting oil E of Table 3 (385 parts by weight) and maleic anhydride (194 parts by weight) were heated to 200° C. in an autoclave under a nitrogen atmosphere and reacted for 10 hours without a catalyst. Then, the unreacted reactants were removed in the same manner as described in Comparative Example 1 to afford 407 parts by weight of a yellowish brown oily reaction product. The saponification value of this reaction product was 369. To the obtained reaction product were added potassium hydroxide (0.97 time the equivalent of the saponification value) and water, and the reaction mixture was saponified to afford a transparent sizing agent related to this invention containing 40% by weight of the solid component (Sizing Agent E-2). The pH of this sizing agent was 8.6.

COMPARATIVE EXAMPLE 5

The starting oil F of Table 3 (352 parts by weight) and maleic anhydride (200 parts by weight) were reacted in the same manner as described in Comparative Example 1 and the unreacted reactants were removed to afford 363 parts by weight of a yellowish brown oily reaction product. The saponification value of this reaction product was 380. This product was saponified in the same manner as described in Comparative Example 1 to give a transparent sizing agent for comparison containing 40% by weight of the solid component (Sizing Agent F). The pH of this sizing agent was 10.0.

COMPARATIVE EXAMPLE 6

The starting oil G of Table 3 (371 parts by weight) and maleic anhydride (188 parts by weight) were reacted in the same manner as described in Comparative Example 1 and the unreacted reactants were removed to afford 358 parts by weight of a yellowish brown oily reaction product. The saponification value of this reaction product was 351. This product was saponified in the same manner as described in Comparative Example 1 to give a transparent sizing agent for comparison containing 40% by weight of the solid component (Sizing Agent G). The pH of this sizing agent was 10.2.

EXAMPLE 4

With respect to the Sizing Agents D, E-1 and E-2 obtained in the above-mentioned Examples 1 to 3 and the Sizing Agents F and G obtained in Comparative Examples 5 and 6, the sizing test and foaming test were carried out. At the same time, as a sizing agent for comparative basis, a commercial reinforced rosin sizing agent was used.

The tests were carried out in the same conditions described in Comparative Example 4, except that the addition amount of the sizing agent in the sizing test was 0.3, 0.6, 0.9 or 1.2% by weight % (as solid component) based on the weight of dry pulp. The results are summarized in Table 4.

TABLE 4

| Sizing Agent | Stockigt Sizing Degree (sec) | | | | Foam Content (% by volume) |
|---|---|---|---|---|---|
| | 0.3* | 0.6* | 0.9* | 1.2* | 0.5* |
| D (This Invention) | 19.8 | 32.5 | 35.2 | 36.5 | 0.10 |
| E-1 (This Invention) | 24.6 | 35.2 | 40.2 | 44.3 | 0.15 |
| E-2 (This Invention) | 23.8 | 34.0 | 40.0 | 44.0 | 0.22 |
| F (Comparative Example) | 21.5 | 32.8 | 37.5 | 39.5 | 0.36 |
| G (Comparative Example) | 4.5 | 21.3 | 28.0 | 30.5 | 0.10 |
| Reinforced Rosin Sizing Agent | 10.7 | 26.0 | 31.2 | 34.0 | 0.30 |

Note:
*Addition amount of sizing agent (% by weight)

The Sizing Agents D, E-1 and E-2 related to this invention show a sizing effect superior to the reinforced rosin sizing agent over a wide range of addition amount, and the amount of the foaming is also less than that of the rosin sizing agent. On the other hand, the Sizing Agent F obtained from the propylene oligomer in which the total content of the oligomers having 11 to 12 carbon atoms is more than 30% by volume in Comparative Example shows a satisfactory sizing effect but the amount of foaming is larger than that of the reinforced rosin sizing agent. The sizing agent G obtained from the propylene oligomer in which the content of the oligomers having 16 or more carbon atoms is more than 50% by volume causes less foaming than that of the reinforced rosin sizing agent but the sizing effect is inferior to it.

EXAMPLE 5

The reaction product obtained in Comparative Example 1 (20 parts by weight), the reaction product obtained in Comparative Example 2 (50 parts by weight) and the reaction product obtained in Comparative Example 3 (30 parts by weight) were mixed. The saponification value of this mixture was 365. The mixture was saponified in the same manner as described in Example 3 to afford a transparent sizing agent related to this invention containing 40% by weight of the solid component (Sizing Agent H). The pH of this sizing agent was 8.7.

EXAMPLE 6

To 30 parts by weight of the emulsified Sizing Agent C (pH 10.1) obtained in Comparative Example 3 were added 20 parts by weight of the Sizing Agent A obtained in Comparative Example 1 and 50 parts by weight of the Sizing Agent B obtained in Comparative Example 2, and the mixture was stirred to afford a transparent sizing agent related to this invention (Sizing Agent I). The pH of this sizing agent was 10.1.

The sizing test and foaming test of Sizing Agents H and I obtained in the above-mentioned Examples 5 and 6 were carried out in the same manner as described in Comparative Example 4 with respect to the case that the addition amount of the sizing agent was 0.5% by weight (as solid component) based on the weight of dry pulp. The results are summarized in Table 5.

TABLE 5

| Sizing Agent | Stockigt Sizing Degree (sec.) | Foam Content (vol %) |
|---|---|---|
| H | 32.5 | 0.20 |
| I | 32.0 | 0.15 |

In this way, both the sizing agent obtained by mixing the reaction product of the propylene oligomer which was fractionally distilled according to carbon number with maleic anhydride followed by saponification and the sizing agent obtained by saponification followed by mixing are included in this invention, and they apparently show an excellent sizing effect and a decreased amount of foaming.

While the invention has been described in detail and with reference to specific embodiments thereof, it will be apparent to one skilled in the art that various changes and modifications can be made therein without departing from the spirit and scope thereof.

What is claimed is:

1. A paper sizing agent, produced by the process comprising the steps of:
   reacting a propylene oligomer having an average molecular weight in the range of 175 to 250 with maleic anhydride under heating in the absence of catalyst, the propylene oligomer is comprised such that it does not substantially contain oligomers having 10 or less carbon atoms and wherein the content of oligomers having 11 to 12 carbon atoms is 0 to 30% by volume, the content of oligomers having 13 to 15 carbon atoms is 20 to 95% by volume and the content of oligomers having 16 to 21 carbon atoms is 5 to 50% by volume;
   allowing the reaction to proceed in order to obtain a reaction product; and
   subjecting the reaction product to alkali saponification.

2. A paper sizing agent as claimed in claim 1, wherein the propylene oligomer has an average molecular weight in the range of 180 to 245.

3. A paper sizing agent as claimed in claim 1, wherein the propylene oligomer includes 0 to 20% by volume of oligomers containing 11 to 12 carbon atoms.

4. A paper sizing agent as claimed in claim 1, wherein the propylene oligomer includes 10 to 40% by volume of oligomers having 16 to 21 carbon atoms.

5. A paper sizing agent as claimed in claim 1, wherein the propylene oligomer and maleic anhydride are reacted in the presence of an inert atmosphere.

6. A paper sizing agent as claimed in claim 4, wherein the reacting is carried out at a temperature in the range of 180° C. to 250° C. for a period of time in the range of 1 to 30 hours.

7. A paper sizing agent as claimed in claim 5, wherein the reacting is carried out at a temperature in the range of 200° C. to 230° C. for a period of time in the range of 3 hours to 20 hours.

8. A paper sizing agent as claimed in claim 1, wherein 0.5 to 3 mol of the maleic anhydride is reacted per mol of the oligomer.

9. A paper sizing agent as claimed in claim 1, wherein the reaction product is a liquid reaction product having a saponification value in the range of 300 to 440.

10. A paper sizing agent as claimed in claim 1, wherein the saponification is carried out in the presence of alkali selected from the group consisting of sodium hydroxide and potassium hydroxide.

11. A paper sizing agent as claimed in claim 8, wherein the alkali is used in the saponification in an amount of 0.8 to 1.2 times the amount needed based on the saponification value of the reaction product.

12. A paper sizing agent as claimed in claim 8, wherein the alkali is used for the saponification in an amount in the range of 0.9 to 1.1 times the amount needed based on the saponification value of the reaction product.

* * * * *